(12) United States Patent
Usui et al.

(10) Patent No.: US 10,545,119 B2
(45) Date of Patent: Jan. 28, 2020

(54) SIGNAL PROCESSING APPARATUS, SERVER, DETECTION SYSTEM, AND SIGNAL PROCESSING METHOD

(71) Applicant: KABUSHIKI KAISHA TOSHIBA, Tokyo (JP)

(72) Inventors: Takashi Usui, Saitama (JP); Kazuo Watabe, Kanagawa (JP); Akihiro Kasahara, Chiba (JP); Takahiro Omori, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 498 days.

(21) Appl. No.: 14/937,218

(22) Filed: Nov. 10, 2015

(65) Prior Publication Data

US 2016/0139084 A1 May 19, 2016

(30) Foreign Application Priority Data

Nov. 18, 2014 (JP) .................................. 2014-233532

(51) Int. Cl.
*G01N 29/14* (2006.01)
*G01N 29/44* (2006.01)

(52) U.S. Cl.
CPC ......... *G01N 29/14* (2013.01); *G01N 29/4445* (2013.01)

(58) Field of Classification Search
CPC .... G01N 29/14; G01N 29/38; G01N 29/4445; G01N 2291/011
See application file for complete search history.

(56) References Cited

U.S. PATENT DOCUMENTS 5,010,503 A * 4/1991 Paton .................... G01N 29/14
702/176
5,293,555 A 3/1994 Anthony
(Continued)

FOREIGN PATENT DOCUMENTS

CN 103149862 A 6/2013
JP 61-134662 6/1986
(Continued)

OTHER PUBLICATIONS

Hura et al. Data and Computer Communication, 2001.*
(Continued)

*Primary Examiner* — Mohammad K Islam
(74) *Attorney, Agent, or Firm* — Finnegan, Henderson, Farabow, Garrett & Dunner, L.L.P.

(57) ABSTRACT

According to an embodiment, a signal processing apparatus includes a receiver, a time information generator, a processor, and a communicator. The receiver receives a voltage signal from a sensor that detects an elastic wave generated from a structure. The time information generator generates time information having a bit length based on a measurement continuing time period of the structure, a propagation velocity of the elastic wave, and a position identification accuracy of a generation source of the elastic wave. The processor generates detection information in which feature amount information that indicates a feature of the voltage signal and the time information that indicates a reception time of the voltage signal are in association with each other. The communicator transmits the detection information to a server.

14 Claims, 14 Drawing Sheets

(56) References Cited

U.S. PATENT DOCUMENTS

| | | | |
|---|---|---|---|
| 7,047,198 B2* | 5/2006 | Ono | G10L 15/22 704/275 |
| 7,080,555 B2 | 7/2006 | Austin et al. | |
| 9,432,298 B1* | 8/2016 | Smith | H04L 49/9057 |
| 2001/0026581 A1* | 10/2001 | Yamanouchi | H04B 1/7077 375/150 |
| 2003/0066692 A1* | 4/2003 | Devige | G06F 3/0433 178/18.04 |
| 2003/0140701 A1* | 7/2003 | O'Brien | G01M 5/0033 73/596 |
| 2010/0008515 A1* | 1/2010 | Fulton | H04R 3/005 381/92 |
| 2010/0034246 A1* | 2/2010 | Hoffmann | G01V 1/22 375/224 |
| 2013/0118261 A1* | 5/2013 | Stothers | G01M 5/0033 73/645 |
| 2013/0191040 A1* | 7/2013 | Yoon | G01N 29/069 702/36 |
| 2014/0260638 A1* | 9/2014 | Hood | G01N 29/14 73/647 |
| 2015/0035950 A1* | 2/2015 | Kontsos | G01N 29/14 348/47 |
| 2016/0041281 A1* | 2/2016 | Takanashi | G01V 1/303 702/6 |
| 2016/0178478 A1* | 6/2016 | Erskine | G01L 25/00 73/593 |

FOREIGN PATENT DOCUMENTS

| | | |
|---|---|---|
| JP | 2-503955 | 11/1990 |
| JP | 5-142105 | 6/1993 |
| JP | 8-128998 | 5/1996 |
| JP | 9-26414 | 1/1997 |
| JP | 3183701 | 7/2001 |
| JP | 2003-536071 A | 12/2003 |
| JP | 2008-501951 | 1/2008 |
| JP | 2011-102700 | 5/2011 |
| JP | 2011-196795 | 10/2011 |

OTHER PUBLICATIONS

Grosse et al., Condition monitoring of concrete structures using wireless sensor networks and MEMS, 2010, pp. 407-418.*

Rasa et al., Long Term Health Monitoring of Anthony Wayne Bridge Main Cable with Acoustic Emission Technique, 2012.*

Hura et al., Data communication (Year: 2001).*

* cited by examiner

| MATERIAL | PROPAGATION VELOCITY v [m/s] |
|---|---|
| IRON | 5950 |
| CONCRETE 1 | 4570 |
| CONCRETE 2 | 3660 |

FIG.11
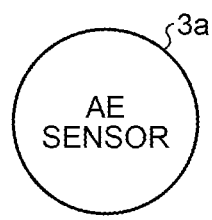
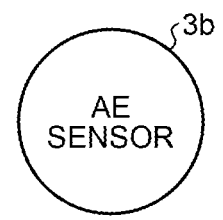
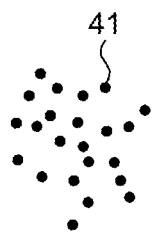
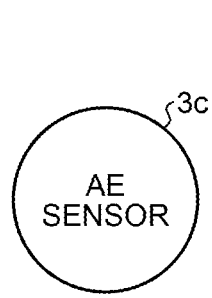
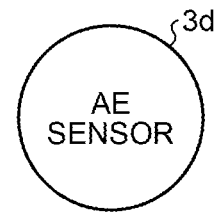

SIGNAL PROCESSING APPARATUS, SERVER, DETECTION SYSTEM, AND SIGNAL PROCESSING METHOD

CROSS-REFERENCE TO RELATED APPLICATION(S)

This application is based upon and claims the benefit of priority from Japanese Patent Application No. 2014-233532, filed on Nov. 18, 2014; the entire contents of which are incorporated herein by reference.

FIELD

An embodiment described herein relates generally to a signal processing apparatus, a server, a detection system, and a signal processing method.

BACKGROUND

As structures such as bridges built in Japan's high-growth period have deteriorated, problems have begun to surface. If an accident happens in such a structure, the damage due to the accident is incalculable. Techniques, thus, have been known that monitor the conditions of the structures. For example, an acoustic emission (AE) technique has been known that detects a damage of such a structure using a highly sensitive sensor that detects an elastic wave generated as a result of internal crack occurrence or internal crack growth.

The acoustic emission is radiation of elastic waves generated with fatigue crack growth in a material. In the AE technique, the elastic waves are detected, as a voltage signal (AE signal), by an AE sensor using a piezoelectric element. The AE signal is detected as a sign before material fracture. The occurrence frequency and the signal intensity of the AE signal are, thus, useful indicators that represent the soundness of a material. Therefore, research has been actively conducted on techniques for detecting signs of the deterioration of the structures using the AE technique. Particularly, for corrosion diagnosis of petroleum tanks and in manufacturing processes of machinery, the detection techniques using the AE technique are widely used mainly in Europe and the United States. The detection techniques using the AE technique have been standardized.

BRIEF DESCRIPTION OF THE DRAWINGS

FIG. 11 is a schematic diagram illustrating an example of display information indicating position information according to the embodiment;

DETAILED DESCRIPTION

According to an embodiment, a signal processing apparatus includes a receiver, a time information generator, a processor, and a communicator. The receiver receives a voltage signal from a sensor that detects an elastic wave generated from a structure. The time information generator generates time information having a bit length based on a measurement continuing time period of the structure, a propagation velocity of the elastic wave, and a position identification accuracy of a generation source of the elastic wave. The processor generates detection information in which feature amount information that indicates a feature of the voltage signal and the time information that indicates a reception time of the voltage signal are in association with each other. The communicator transmits the detection information to a server.

The following describes a signal processing apparatus, a server, a detection system, and a signal processing method according to an embodiment in detail with reference to the accompanying drawings.

Figure 1:
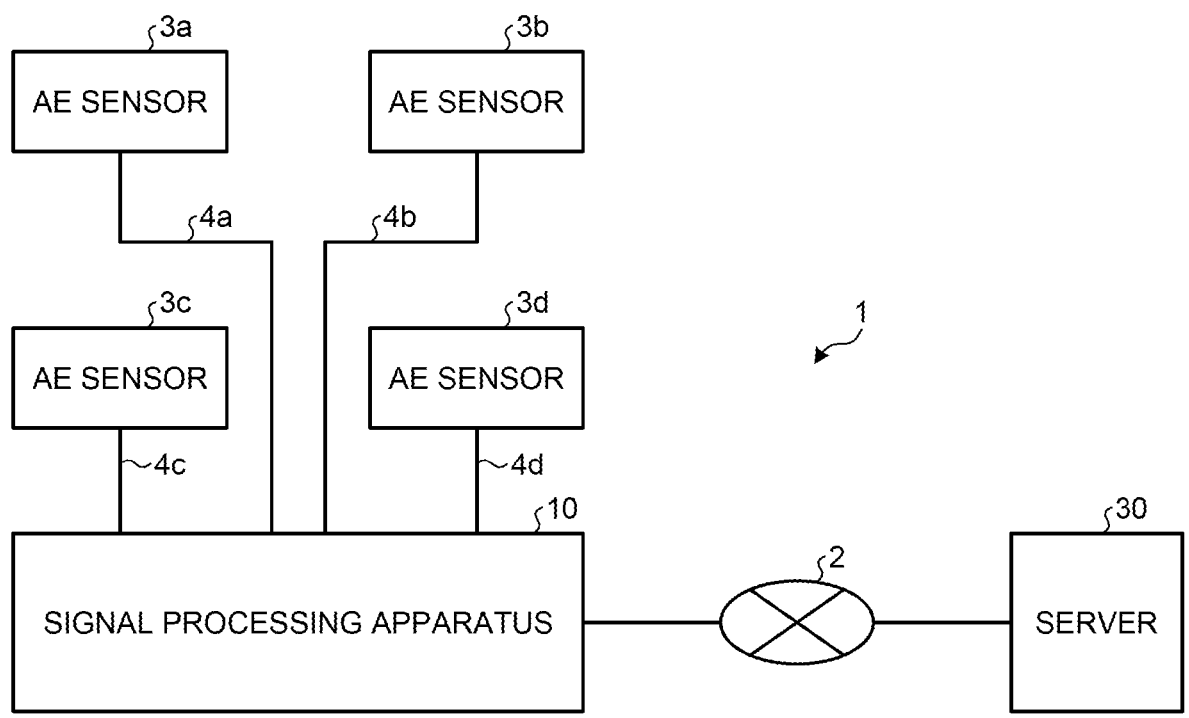
FIG. 1 is a schematic diagram illustrating an exemplary structure of a detection system according to an embodiment.

FIG. 1 is a schematic diagram illustrating an exemplary structure of the detection system according to the embodiment. A detection system 1 according to the embodiment includes AE sensors 3a to 3d, a signal processing apparatus 10, and a server 30. The AE sensors 3a, 3b, 3c, and 3d are connected to the signal processing apparatus 10 with cables 4a, 4b, 4c, and 4d, respectively. The signal processing apparatus 10 and the server 30 are connected via a network 2. In the following description, the AE sensors 3a to 3d are simply described as an AE sensor 3 when they are not differentiated from one another. Likewise, the cables 4a to 4d are simply described as a cable 4 when they are not differentiated from one another.

The cable 4 may be changed to a wireless connection. The network 2 may employ a wireless or a wire-based communication technique, or a combination of a wireless and a wire-based communication techniques. A plurality of signal processing apparatuses 10 may be connected to the server 30. The number of AE sensors 3 connected to the signal processing apparatus 10 is not limited to four. Any number of AE sensors 3 may be connected to the signal processing apparatus 10 as long as the number satisfies the number of AE sensors 3 necessary for identifying (locating) the position of a generation source of an elastic wave. The details of a method for identifying the generation source of an elastic wave are described later.

The AE sensor 3 is installed on a structure such as a bridge. The AE sensor 3 detects an elastic wave generated from the structure and converts the elastic wave into an AE signal (voltage signal).

Specifically, the AE sensor 3 uses a piezoelectric element having a sensitivity ranging from 10 kHz to 1 MHz, for example. Any type can be used for the AE sensor 3. Examples of the type of the AE sensor 3 include a resonance type that has a resonance peak in a frequency range and a wide range type that suppresses resonance. The AE sensor 3 may include a preamplifier. The AE sensor 3 may employ any type of detection method. Examples of the detection method include a voltage output type, a variable resistance type, and an electrostatic capacitance type.

The AE sensor 3 transmits the AE signal to the signal processing apparatus 10. The signal processing apparatus 10 processes the AE signal received from the AE sensor 3 and transmits detection information, which is described later, to the server 30. The following describes an exemplary structure of the signal processing apparatus 10.

Figure 2:
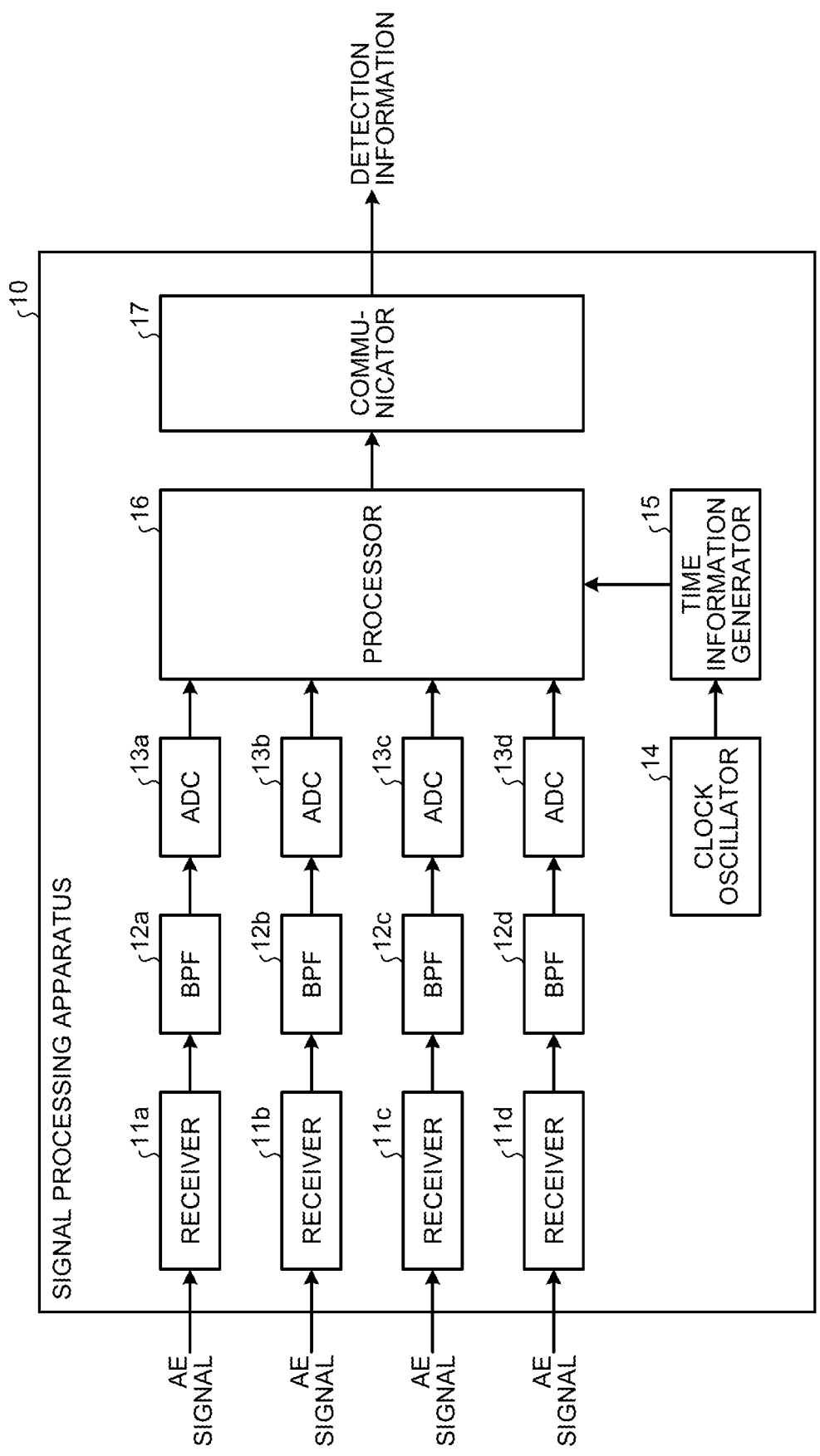
FIG. 2 is a schematic diagram illustrating an exemplary structure of a signal processing apparatus according to the embodiment.

FIG. 2 is a schematic diagram illustrating an exemplary structure of the signal processing apparatus 10 according to the embodiment. The signal processing apparatus 10 according to the embodiment includes receivers 11a to 11d, band pass filters (BPFs) 12a to 12d, A/D converters (ADCs) 13a to 13d, a clock oscillator 14, a time information generator 15, a processor 16, and a communicator 17.

The receivers 11a to 11d are simply described as a receiver 11 when they are not differentiated from one another. The BPFs 12a to 12d are simply described as a BPF 12 when they are not differentiated from one another. The ADCs 13a to 13d are simply described as an ADC 13 when they are not differentiated from one another.

When receiving the AE signal from the AE sensor 3, the receiver 11 inputs the received AE signal to the BPF 12.

When receiving the AE signal from the receiver 11, the BPF 12 removes noise components outside a signal band from the AE signal. The BPF 12 inputs the AE signal from which noise components are removed to the ADC 13.

When receiving, from the BPF 12, the AE signal from which noise components are removed, the ADC 13 quantizes the AE signal from which noise components are removed so as to convert the AE signal into a digital AE signal. The ADC 13 inputs the digital AE signal to the processor 16.

The clock oscillator 14 generates a clock signal. The clock oscillator 14 is a crystal oscillator, for example. The clock oscillator 14 inputs the clock signal to the time information generator 15.

The time information generator 15 receives the clock signal from the clock oscillator 14. The time information generator 15 generates time information using the clock signal. The time information generator 15 is a counter including a register, for example. The time information generator 15 counts edges of the clock signal and stores the accumulated count value from when power is turned on to the signal processing apparatus 10 in the register as the time information.

A bit length b of the time information (register) is determined, on the basis of a measurement continuing time period y of a structure and time resolution power dt, to an integer b that is equal to or larger than one and satisfies the relation of $b \geq \log_2 (y/dt)$. The time resolution power dt is determined as follows: $dt=dr/v$ where v is a propagation velocity of an elastic wave and dr is a position identification accuracy of the generation source of the elastic wave. The position identification accuracy of the generation source of the elastic wave, thus, can be set to any range, thereby making it possible for the signal processing apparatus 10 to necessarily and sufficiently identify the position.

For example, when the material of the structure is iron, the propagation velocity v of the elastic wave is 5950 m/s. In this case, when the position identification accuracy of the generation source of the elastic wave is 10 mm, $dt=0.1/5980=1.68 \times 10^{-6}$ seconds (round up to two decimal places). When the number of continuous measurement years is 100, $y=100 \times 365 \times 24 \times 60 \times 60=3153600000$ seconds. The bit length b of the time information (register) is calculated as a minimum positive integer that satisfies the relation of $b \geq \log_2 (y/dt)=\log_2 (3153600000/1.68 \times 10^{-6})$. The bit length b is, thus, equal to or larger than 51 bits.

In typical wireless modules, data transmission is basically performed on a byte basis using transmission packets. When the communicator 17, which is described later, is achieved by a typical wireless module, it is necessary that the bit length b of the time information (register) is a multiple of eight. The bit length b of the time information (register) is determined to the lowest multiple of eight that satisfies $b \geq 51$ bits. The bit length b is, thus, determined to 56 bits=7 bytes. As a result, a typical wireless module can be used for transmission of the time information.

Figure 3:
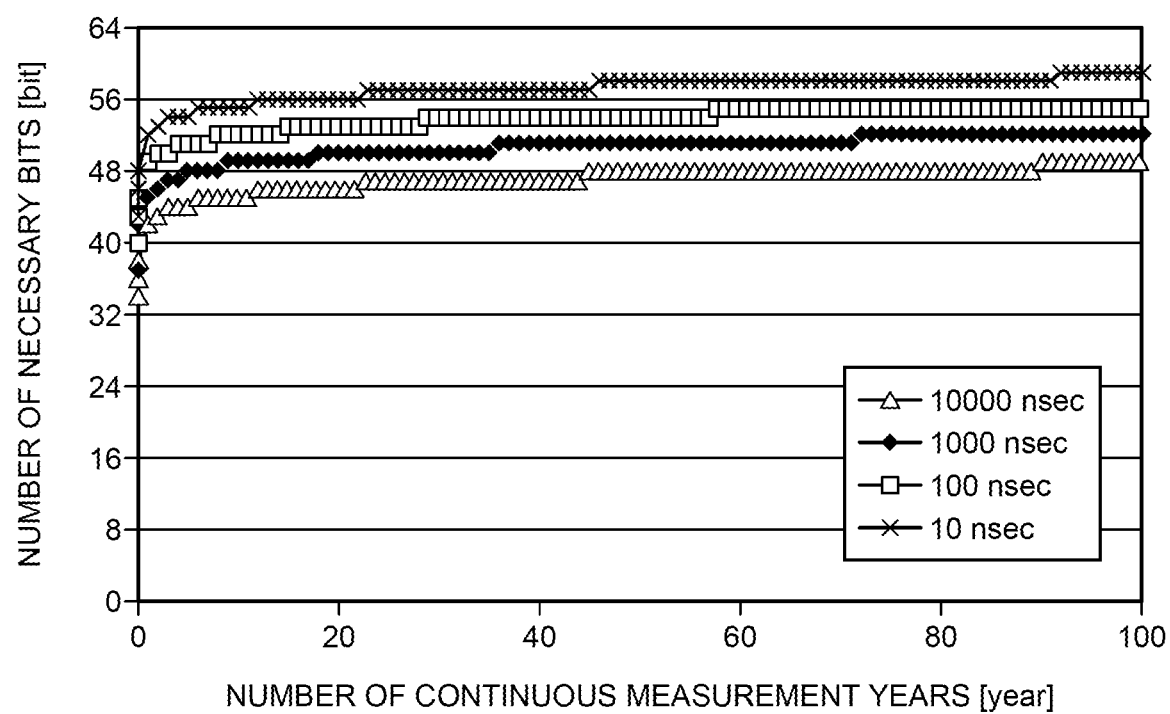
FIG. 3 is a graph illustrating a relation between the number of bits of time information and the number of continuous measurement years.

FIG. 3 is a graph illustrating a relation between the number of bits of time information and the number of continuous measurement years. The smaller the time resolution power dt is, the larger the number of bits of time information necessary for being stored is. The longer the number of continuous measurement years is, the larger the number of bits of time information necessary for being stored is.

The following describes an exemplary structure of the processor 16.

Figure 4:
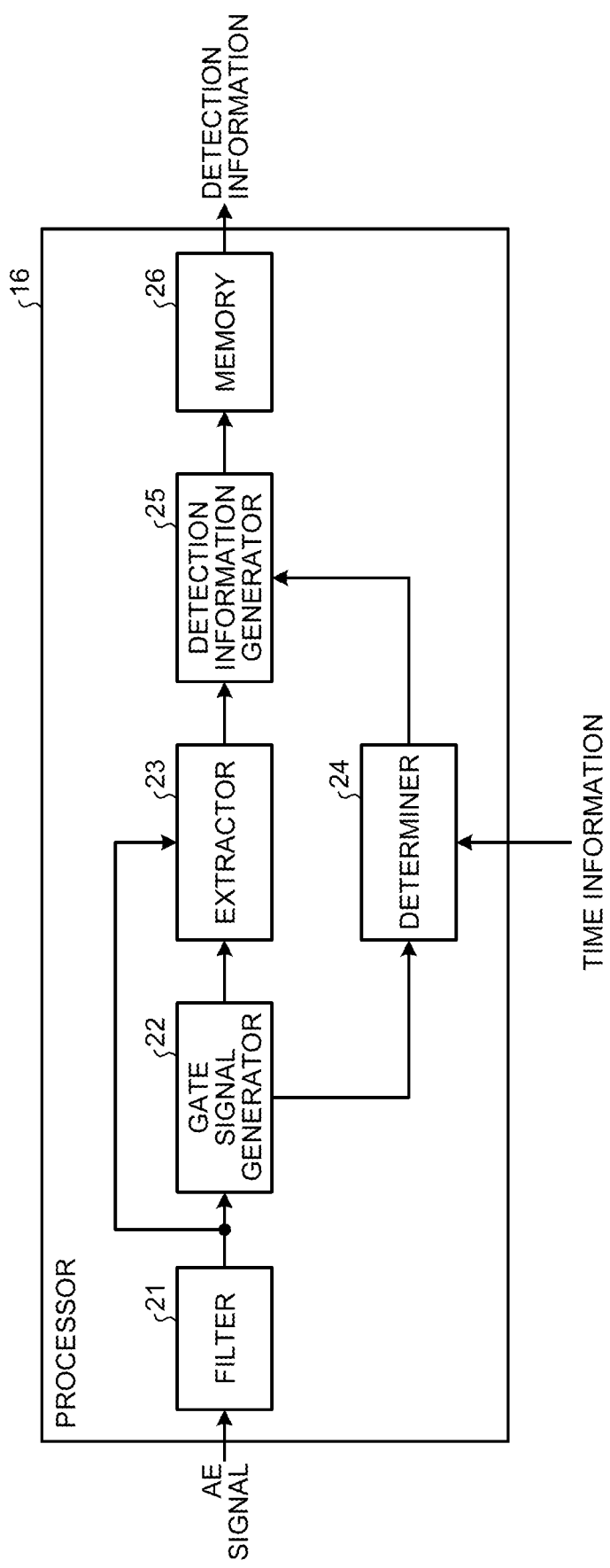
FIG. 4 is a schematic diagram illustrating an exemplary structure of a processor according to the embodiment.

FIG. 4 is a schematic diagram illustrating an exemplary structure of the processor 16 according to the embodiment. The processor 16 according to the embodiment includes a filter 21, a gate signal generator 22, an extractor 23, a determiner 24, a detection information generator 25, and a memory 26.

When receiving the digital AE signal from the ADC 13, the filter 21 inputs the AE signal in a certain frequency range to the gate signal generator 22 and the extractor 23.

The gate signal generator 22 receives the AE signal in the certain frequency range from the filter 21. The gate signal generator 22 generates a gate signal that indicates whether the waveform of the AE signal continues.

The gate signal generator 22 is achieved by an envelope detector and a comparator, for example. The envelope detector detects the envelope of the AE signal and the comparator determines whether the envelope of the AE signal is equal to or larger than a certain threshold. When the envelope of the AE signal is equal to or larger than the certain threshold, the gate signal generator 22 inputs, to the extractor 23 and the determiner 24, a gate signal (of a high level) indicating that the waveform of the AE signal continues. When the envelope of the AE signal is smaller than the certain threshold, the gate signal generator 22 inputs, to the extractor 23 and the determiner 24, a gate signal (of a low level) indicating that the waveform of the AE signal does not continue.

The extractor 23 receives the AE signal in the certain frequency range from the filter 21 and the gate signal from the gate signal generator 22. The extractor 23 extracts feature amount information when the waveform of the AE signal continues on the basis of the gate signal. The feature amount information indicates the feature of the AE signal. Examples of the feature amount information include an amplitude (mV) of the waveform of the AE signal, a rise time period (µs) of the gate signal, a continuing time period (µs) of the gate signal, the zero-crossing counts (times) of the AE signal, energy (in an arbitrary unit) of the waveform of the AE signal, and a frequency (Hz) of the AE signal. The extractor 23 inputs the feature amount information to the detection information generator 25.

The determiner 24 receives the time information from the time information generator 15 and the gate signal from the gate signal generator 22. The determiner 24 determines a reception time on the basis of the time information and the gate signal. Specifically, the determiner 24 determines, as the reception time of the AE signal, the time information indicating a rise time of the gate signal. The determiner 24 inputs the time information indicating the reception time to the detection information generator 25.

The detection information generator 25 receives the feature amount information from the extractor 23 and the time information indicating the reception time from the determiner 24. The detection information generator 25 generates detection information in which the feature amount information indicating the feature of the AE signal and the time information indicating the reception time of the AE signal are in association with each other. The detection information generator 25 stores the detection information in the memory 26. The memory 26 is a dual port random access memory (RAM), for example.

Figure 5:
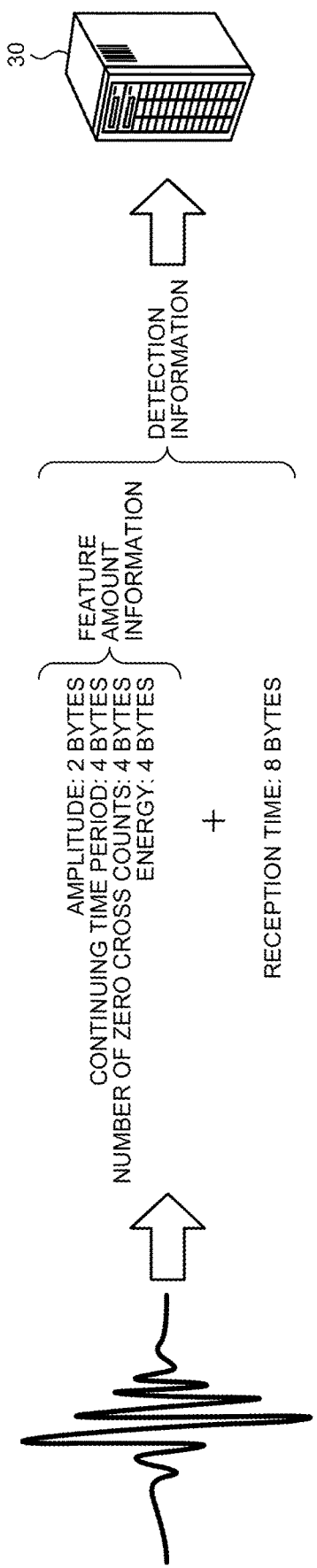
FIG. 5 is a schematic diagram illustrating an example of detection information according to the embodiment.

FIG. 5 is a schematic diagram illustrating an example of the detection information according to the embodiment. The example in FIG. 5 illustrates a case where the detection information of 22 bytes is generated. The detection information includes the feature amount information of 14 bytes and the time information of 8 bytes indicating the reception time. The feature amount information includes the amplitude of 2 bytes, the continuing time period of 4 bytes, the zero-crossing counts of 4 bytes, and energy of 4 bytes. The feature amount information is not limited to the example illustrated in FIG. 5. Any information that indicates the feature of the AE signal is used for the feature amount information.

Referring back to FIG. 2, the communicator 17 reads out the detection information from the memory 26 of the processor 16. The communicator 17 transmits the detection information to the server 30 at certain timing by wireless communication. As for the frequency band of the wireless communication, what is called an industry science medical (ISM) band such as 2.4 GHz and 915 MHz bands (in Japan, 915 MHz to 928 MHz) is used, for example. The communicator 17 may transmit the detection information directly to the server 30 without using the memory 26. The communicator 17 may employ a wire-based communication scheme.

The following describes hardware of the signal processing apparatus 10. Power of the signal processing apparatus 10 is supplied from an external power source, a primary battery, a secondary battery, a solar battery, or an energy harvester, for example. The energy harvester is a vibration power generation module, for example. The signal processing apparatus 10 is achieved by an analog circuit and a digital circuit. The power source of the analog circuit is an insulated switching power source. The digital AE signal quantized by the ADC 13 is input to the processor 16 via a digital isolator. This makes it possible to separate an analog ground and a digital ground, thereby preventing noise from propagating therebetween. The analog ground and the digital ground may be short-circuited at one point if necessary.

The processor 16 is achieved by a field programmable gate array (FPGA), for example. The use of a non-volatile FPGA can reduce standby power consumption. The processor 16 may be achieved by a dedicated large scale integration (LSI).

The signal processing apparatus 10 includes a non-volatile random access memory (NVRAM) used by being mounted on a substrate, such as a flash memory or a magnetic random access memory (MRAM). Storing threshold information in the non-volatile memory used by being mounted on a substrate makes it unnecessary to reset the information when power is lost. Instead of the non-volatile memory used by being mounted on a substrate, a removable memory such as a flash memory may be used. For example, a memory card such as an SD card (registered trademark) is inserted in the signal processing apparatus 10 and the detection information may be stored in the memory card. The server 30 reads the memory card, thereby making it possible to monitor a structure at a place where the wires communication cannot be used.

The signal processing apparatus 10 includes a push switch that turns on or off a contact. The time information generator 15 resets the time information to a certain initial value in accordance with the switching of the on and off of the contact of the push switch.

The following describes an exemplary structure of the server 30.

Figure 6:
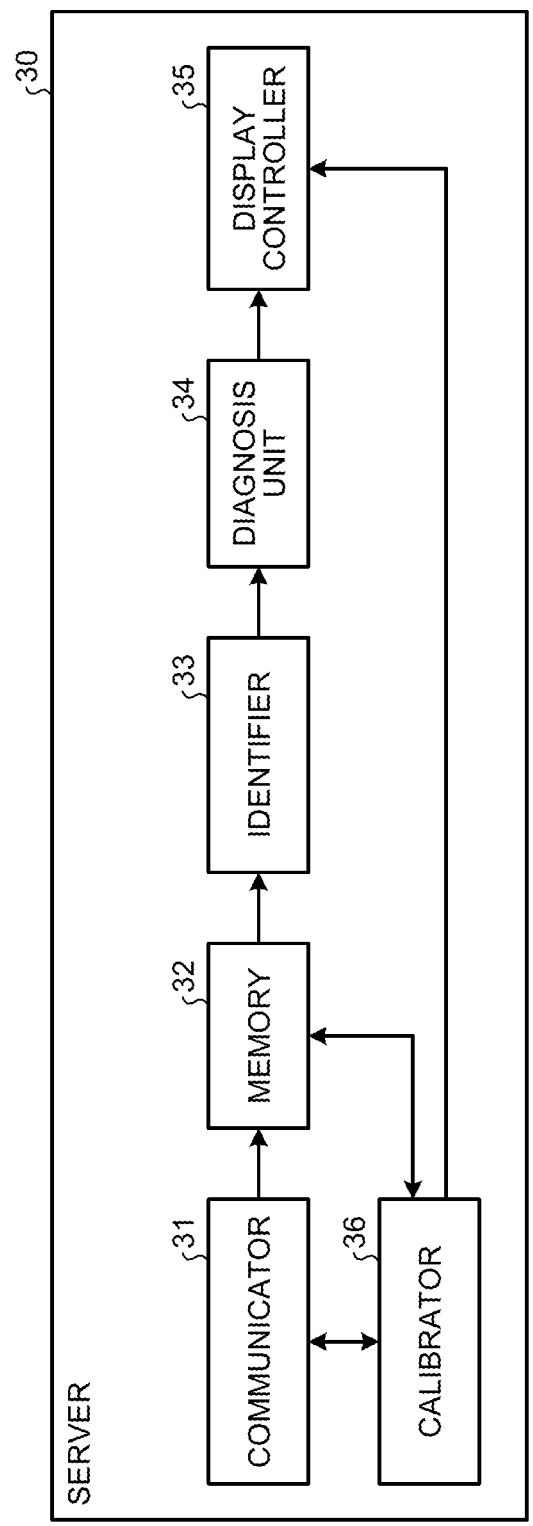
FIG. 6 is a schematic diagram illustrating an exemplary structure of a server according to the embodiment.

FIG. 6 is a schematic diagram illustrating an exemplary structure of the server 30 according to the embodiment. The server 30 according to the embodiment includes a communicator 31, a memory 32, an identifier 33, a diagnosis unit 34, a display controller 35, and a calibrator 36.

The communicator 31 receives the detection information from the signal processing apparatus 10. The communicator 31 stores the detection information in the memory 32.

The memory 32 stores therein initial installation position information (installation position information) about the AE sensors 3a to 3d, the detection information transmitted from the signal processing apparatus 10, and propagation velocity information. The initial installation position information may be updated to the installation position information in which displacements of the AE sensors 3a to 3d are taken into consideration by the calibrator 36, which is described later. The details of the propagation velocity information are described later.

The identifier 33 reads out the detection information from the memory 32 at certain timing. The identifier 33 identifies the position information about the generation source of an elastic wave on the basis of the detection information.

Specifically, the identifier 33 calculates similarities of the pieces of feature amount information included in the respective pieces of detection information, and classifies the pieces of detection information into groups on the basis of whether the similarity of the feature amount information is equal to or larger than a certain threshold. The identifier 33 recognizes the detection information included in the same group as the detection information about the same generation source.

The similarity is determined by a distance between the pieces of feature amount information. The smaller the distance between the pieces of feature amount information is, the larger the similarity is. The identifier 33 calculates the distance between the pieces of feature amount information using a certain distance function. The distance function is a function that calculates a standard Euclidean distance, a Minkowski distance, or a Mahalanobis distance, for example. Particularly, the Mahalanobis distance makes it possible to calculate a distance taking into consideration correlation between the pieces of feature amount information, thereby making it possible to increase a classification accuracy of the groups.

The identifier 33 calculates time difference information about the reception times of the AE signals among the four AE sensors by comparing the respective pieces of time information associated with the corresponding pieces of feature amount information (the pieces of feature amount information included in the pieces of detection information classified into the same group) each having a similarity equal to or larger than a certain threshold. The identifier 33 identifies the position information about the generation source of the elastic wave on the basis of the position information about the four AE sensors 3, the time difference information, and the propagation velocity of the elastic wave. The following describes the propagation velocity of elastic wave.

The propagation velocity v of elastic wave propagating in a material is represented the following equation (1).

$$v = \sqrt{\frac{K}{\rho_0}} \quad (1)$$

where K (Pa) is the volume elasticity modulus of the material and $\rho_0$ (kg/m³) is the density of the material.

The propagation velocity v of elastic wave propagating in a structure (three-dimensional body) is represented by the following expression (2) taking into account a shearing modulus G of the material.

$$v = \sqrt{\frac{1}{\rho_0} \cdot \left(K + \frac{4}{3}G\right)} \quad (2)$$

The propagation velocity of elastic wave is determined by the physical properties inherent to a material. For example, the propagation velocity information, which is obtained by being preliminarily calculated for each material (material of a structure), is stored in the memory 32 as a look-up table. This look-up table makes it possible for the identifier 33 to select an appropriate propagation velocity according to the material of the structure from the look-up table.

Figures 7, 8:
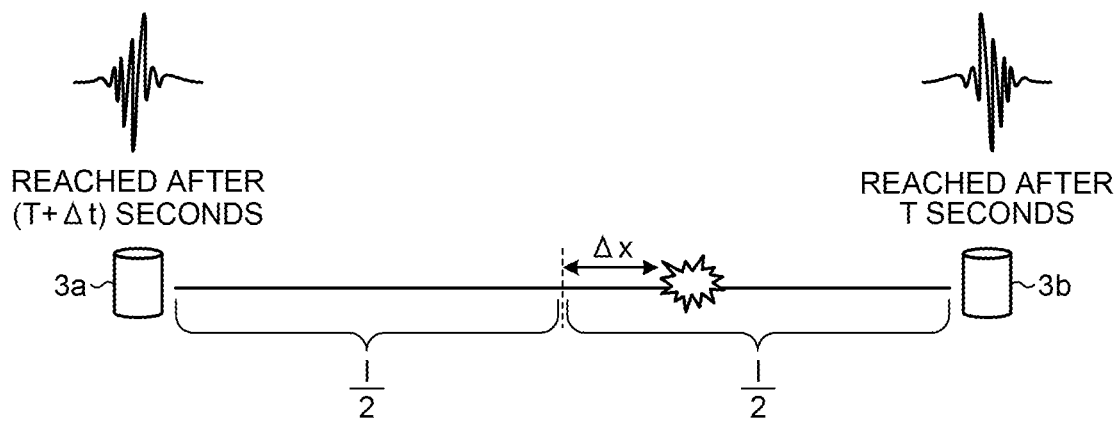
FIG. 7 is a schematic diagram illustrating an example of propagation velocity information according to the embodiment.
FIG. 8 is a schematic diagram to explain an exemplary position identification method (in a one-dimensional arrangement) according to the embodiment.

FIG. 7 is a schematic diagram illustrating an example of the propagation velocity information according to the embodiment. FIG. 7 illustrates an example where the propagation velocity information is stored as a look-up table. For example, when the material of the structure is iron, the propagation velocity v is 5950 m/s.

The following describes a method for identifying the position of the generation source of an elastic wave by the identifier 33. The method is described in detail on the basis of a one-dimensional arrangement for simple explanation. The identification principle is the same as those in a two-dimensional and a three-dimensional arrangement.

FIG. 8 is a schematic diagram to explain an exemplary position identification method (in the one-dimensional arrangement) according to the embodiment. In the example, a crack occurs in a structure between the AE sensors 3a and 3b, and the AE sensors 3a and 3b detect an elastic wave due to the crack.

The distance between the AE sensors 3a and 3b is 1. The distance from the midpoint between the AE sensors 3a and 3b to the crack is Δx. When the AE sensor 3b detects the elastic wave after T seconds from the crack occurrence while the AE sensor 3a detects the elastic wave after (T+Δt) seconds from the crack occurrence, Δt can be represented by the following expression (3).

$$\Delta t = \left(\left(\frac{1}{2} + \Delta x\right) - \left(\frac{1}{2} - \Delta x\right)\right) \bigg/ v = 2\Delta x/v \quad (3)$$

When the distance 1 between the AE sensors 3a and 3b and the propagation velocity v of the elastic wave are known, the identifier 33 calculates the time difference information Δt, and then can calculate the distance Δx from the midpoint between the AE sensors 3a and 3b to the crack using the expression (3). In this way, the identifier 33 can identify the position information about the crack (generation source of the elastic wave) from the time difference information Δt.

The following simply describes a position identification method on the basis of a two-dimensional arrangement.

Figure 9:
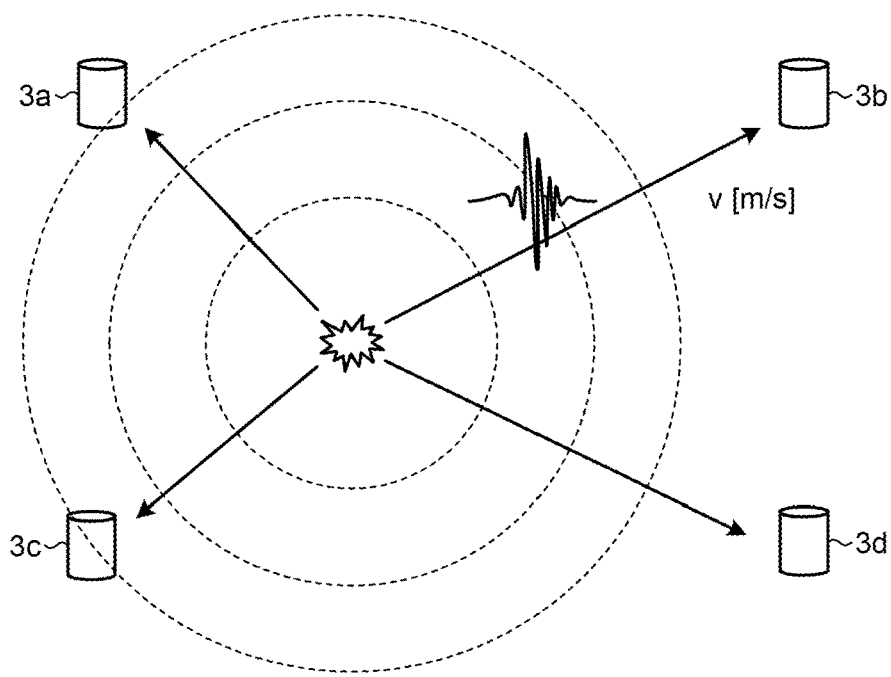
FIG. 9 is a schematic diagram to explain an exemplary position identification method (in a two-dimensional arrangement) according to the embodiment.
Figure 10:
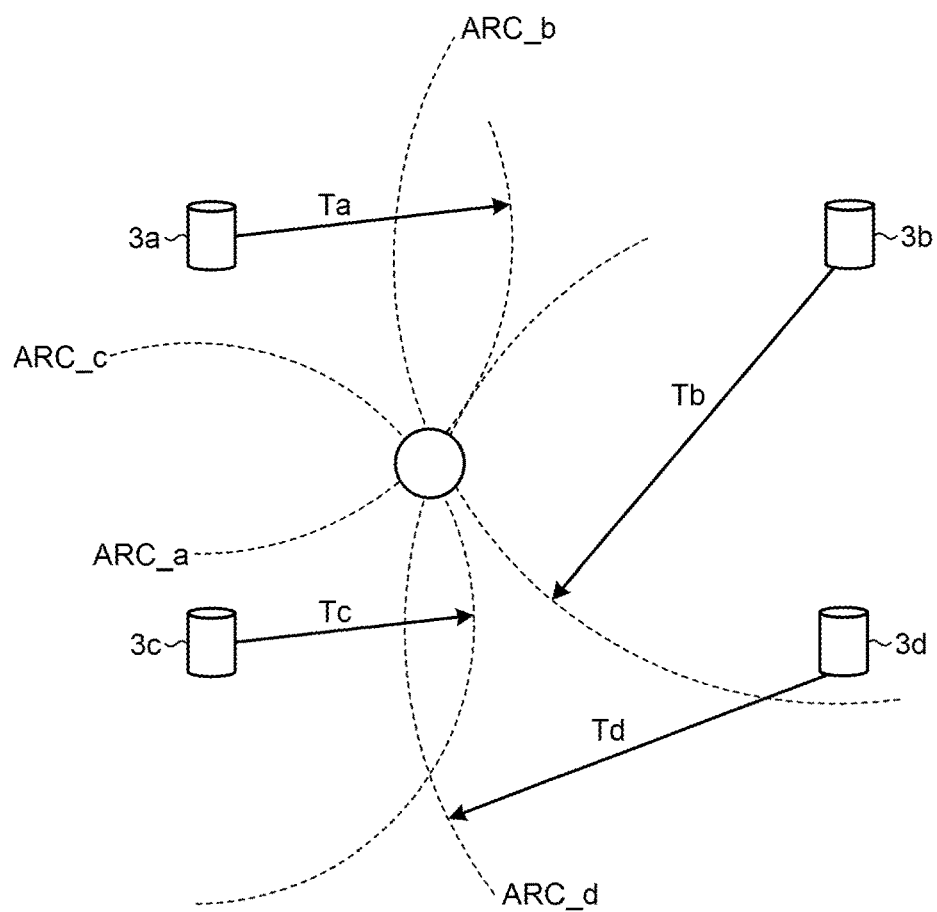
FIG. 10 is a schematic diagram to explain the exemplary position identification method (in the two-dimensional arrangement) according to the embodiment.

FIGS. 9 and 10 are schematic diagrams to explain an exemplary position identification method (in the two-dimensional arrangement) according to the embodiment. FIG. 9 illustrates a case where a crack occurs in a structure and an elastic wave due to the crack occurrence reaches the AE sensors 3a to 3d with the propagation velocity v (m/s). The times when the elastic wave reaches the AE sensor 3a to the AE sensor 3d differ from each other. When a time difference in reception time of the elastic wave is known, it can be estimated that the generation source of the elastic wave is on a circle ARC_a (radius Ta), a circle ARC_b (radius Tb), a circle ARC_c (radius Tc), and a circle ARC_d (radius Td). The circles ARC-a, ARC-b, ARC-c, and ARC-d have the AE sensors 3a, 3b, 3c, and 3d as the centers, respectively. The identifier 33, thus, can identify the intersection of the circles ARC-a to ARC-d as the position information about the generation source of the elastic wave.

In general, the position of the generation source of elastic wave can be identified using the AE sensors 3 the number of which is the number of dimensions plus one. The position of the generation source of elastic wave can thus be identified using the four AE sensors 3 in the three dimensional arrangement. The larger the number of AE sensors 3 is, the further the identification accuracy of the position information can be increased.

When the identified position information is out of a certain observation range (when the identified position information does not satisfy a certain threshold), the identifier 33 performs noise processing to remove, as noise, the feature amount information included in the detection information used for the identification. The noise processing is performed by the identifier 33 of the server 30, thereby making it possible to flexibly change a threshold condition used for the determination in the noise processing. The installation states of the AE sensor 3, the conditions of the structure to be measured, and weather conditions can be flexibly changed, thereby making it possible for the identifier 33 to more effectively remove noise.

Referring back to FIG. 6, the identifier 33 inputs the detection information and the position information to the diagnosis unit 34.

The diagnosis unit 34 receives the detection information and the position information from the identifier 33. The diagnosis unit 34 diagnoses the deterioration of the structure on the basis of the detection information and the position information. The diagnosis unit 34 diagnoses the deterioration of the structure by determining whether the generation source is present the cumulative energy of elastic wave of which is equal to or larger than a certain threshold, for example. The diagnosis unit 34 generates diagnosis result information that indicates the diagnosis result. The diagnosis unit 34 inputs the detection information, the position information, and the diagnosis result information to the display controller 35.

The display controller 35 receives the detection information, the position information, and the diagnosis result information from the diagnosis unit 34. The display controller 35 displays display information based on the detection information, the position information, and the diagnosis result information on a display device, which is not illustrated in FIG. 6.

FIG. 11 is a schematic diagram illustrating an example of the display information indicating the position information according to the embodiment. FIG. 11 illustrates a case where the generation source of an elastic wave is displayed by position information 41, for example.

Figure 12:
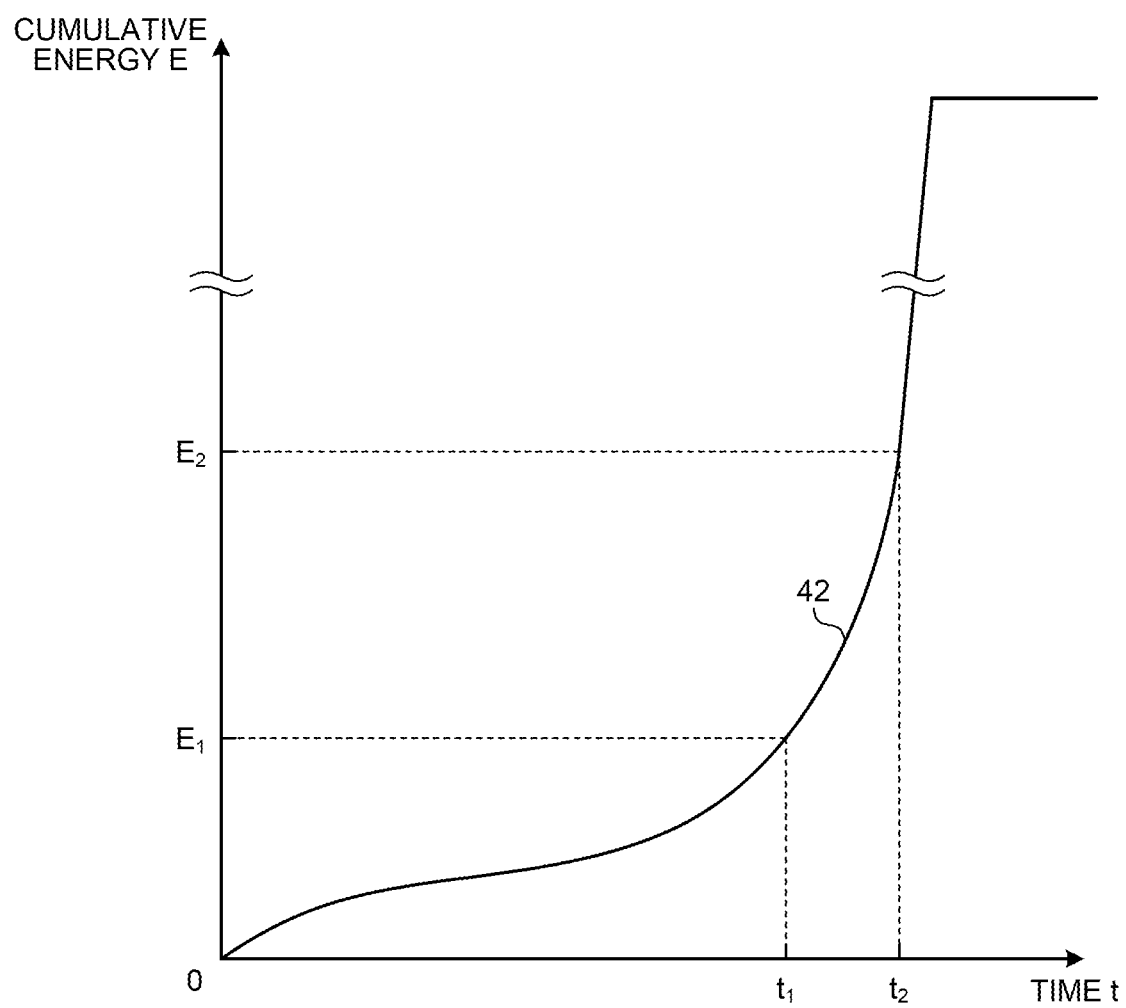
FIG. 12 is a schematic diagram illustrating an example of the display information indicating cumulative energy according to the embodiment.

FIG. 12 is a schematic diagram illustrating an example of the display information indicating the cumulative energy according to the embodiment. FIG. 12 illustrates a case where the cumulative energy is displayed with a curve 42. When the display information illustrated in FIG. 11 is illustrated and an input is made that indicates the selection of the position information 41, for example, the display controller 35 performs control such that the display information illustrated in FIG. 12 is displayed. When a user designates a selection range on the screen on which the display information illustrated in FIG. 11 is displayed, the cumulative energy of elastic waves included in the selection range is displayed with the curve 42, thereby making it possible to readily know the characteristic in the selection range. The selection range is set inside a rectangle having a diagonal line from the drag position to the drop position, both of which positions are designated by drag-and-drop operation using a mouse, or inside a circle inscribed in the rectangle, for example, thereby making it possible to further improve the operability.

Cumulative energy $E_1$ is used as a threshold when the diagnosis unit 34 diagnoses a deterioration condition of a structure. The diagnosis unit 34 requests the display controller 35 to display a warning that indicates that the degree of deterioration is large, for example, at time $t_1$ when the cumulative energy becomes $E_1$. This warning makes it possible for the manager, for example, of the structure to know a high occurrence possibility of a fracture in the structure before the fracture and other damage occur in the structure due to further deterioration of the structure. The example in FIG. 12 illustrates a case where a fracture occurs in the structure at time $t_2$. The cumulative energy E is sharply increased after cumulative energy $E_2$ because of the shock of the fracture in the structure. When the state of the structure becomes stable after the fracture, no elastic wave is generated and the cumulative energy E is constant.

Referring back to FIG. 6, the calibrator 36 calibrates the respective pieces of installation position information about the AE sensors 3a to 3d. Specifically, the calibrator 36 transmits, to the signal processing apparatus 10 via the communicator 31, a calibration request that causes any one of the AE sensors 3 to operate as a vibration generation source.

Figure 13:
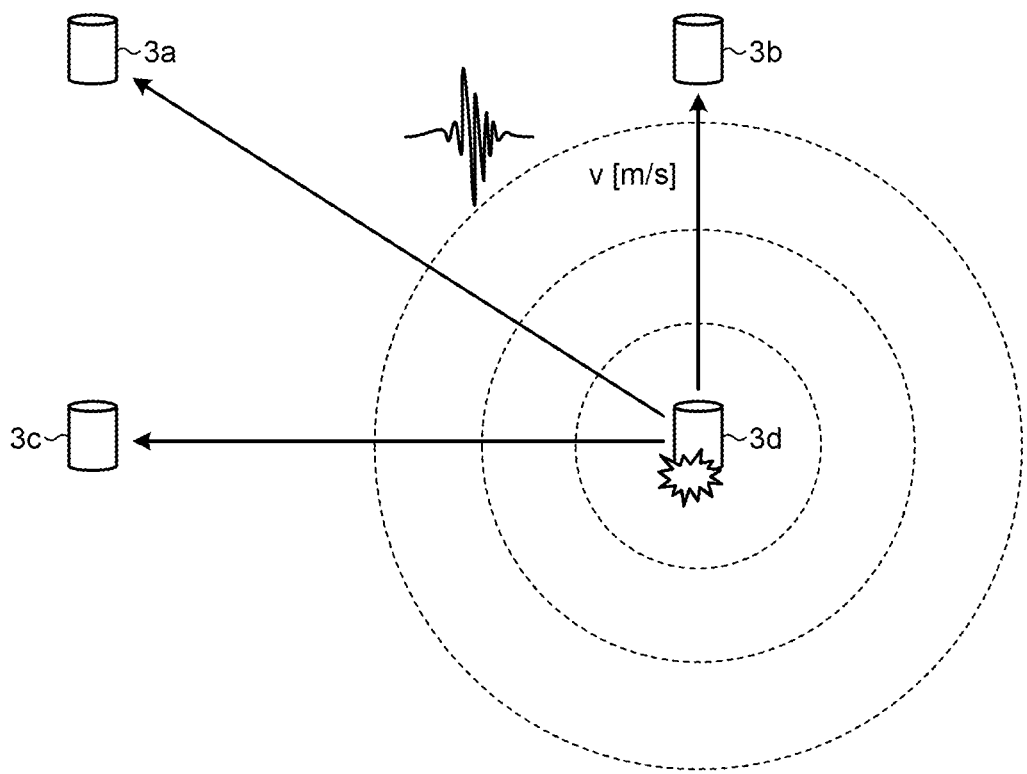
FIG. 13 is a schematic diagram to explain an example of a position calibration method according to the embodiment.

FIG. 13 is a schematic diagram to explain an example of a position calibration method according to the embodiment. FIG. 13 illustrates a case where the signal processing apparatus 10 causes the AE sensor 3d to operate as the vibration generation source when receiving the calibration request from the server 30. Specifically, the AE sensor 3d generates an elastic wave having a certain identification pattern at certain timing. The AE sensors 3a to 3c detect the elastic wave at time differences corresponding to the respective distances from the AE sensor 3d. The signal processing apparatus 10 transmits, to the server 30, the detection information including the feature amount information about the AE signal indicating the elastic wave and the time information indicating the reception time of the AE signal indicating the elastic wave. The calibrator 36 of the server 30 determines whether the pattern of elastic wave is the certain identification pattern. When it is determined that the pattern of the elastic wave is the certain identification pattern, the calibrator 36 calculates the time difference information. This results in an effect of removing noise. When the time difference information differs from the time difference information assumed from the initial installation position information at the installation stored in the memory 32, the calibrator 36 requests the display controller 35 to display information that notifies a user of the possibility of the position of the AE sensor 3 being shifted.

The calibrator 36 may calculate relative positional relations among the AE sensors 3a to 3d by performing the process described above by sequentially switching the AE sensors 3a to 3d as the vibration generation source, and update the initial installation position information about the AE sensors 3a to 3d stored in the memory 32.

The calibrator 36 may calibrate the value of propagation velocity of elastic wave corresponding to a material of a structure stored in the memory 32 in a form of a look-up table (refer to FIG. 7) by causing the AE sensor 3 to operate as the vibration generation source.

The following describes a signal processing method according to the embodiment.

Figure 14:
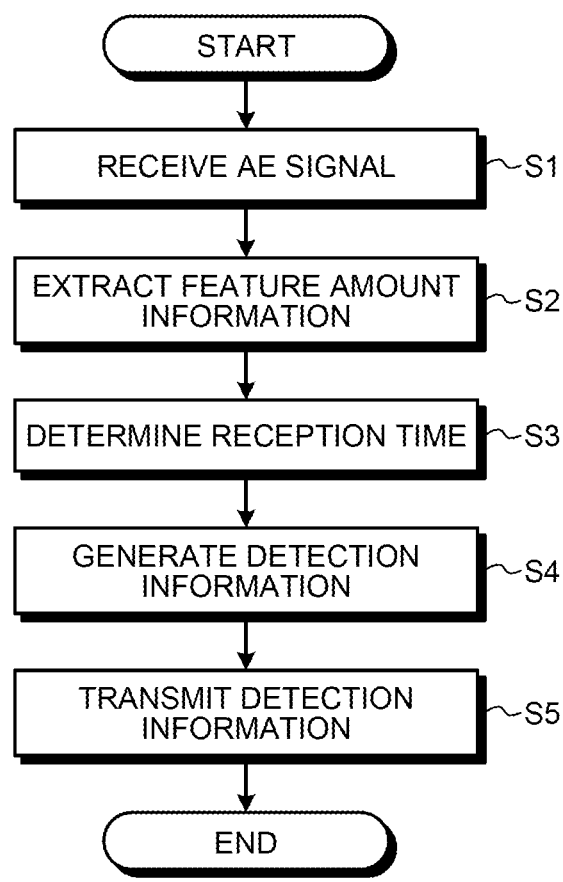
FIG. 14 is a flowchart illustrating exemplary operation of the signal processing apparatus according to the embodiment.

FIG. 14 is a flowchart illustrating an operation example of the signal processing apparatus 10 according to the embodiment. The receiver 11 receives the AE signal from the AE sensor 3 (step S1). The extractor 23 extracts the feature amount information when the waveform of the AE signal continues on the basis of the gate signal (step S2). The determiner 24 determines, as the reception time of the AE signal, the time information indicating the rise time of the gate signal (step S3). The detection information generator 25 generates the detection information in which the feature amount information indicating the feature of the AE signal and the time information indicating the reception time of the AE signal are in association with each other (step S4). The communicator 17 transmits the detection information to the server 30 at certain timing by wireless communication (step S5).

Figure 15:
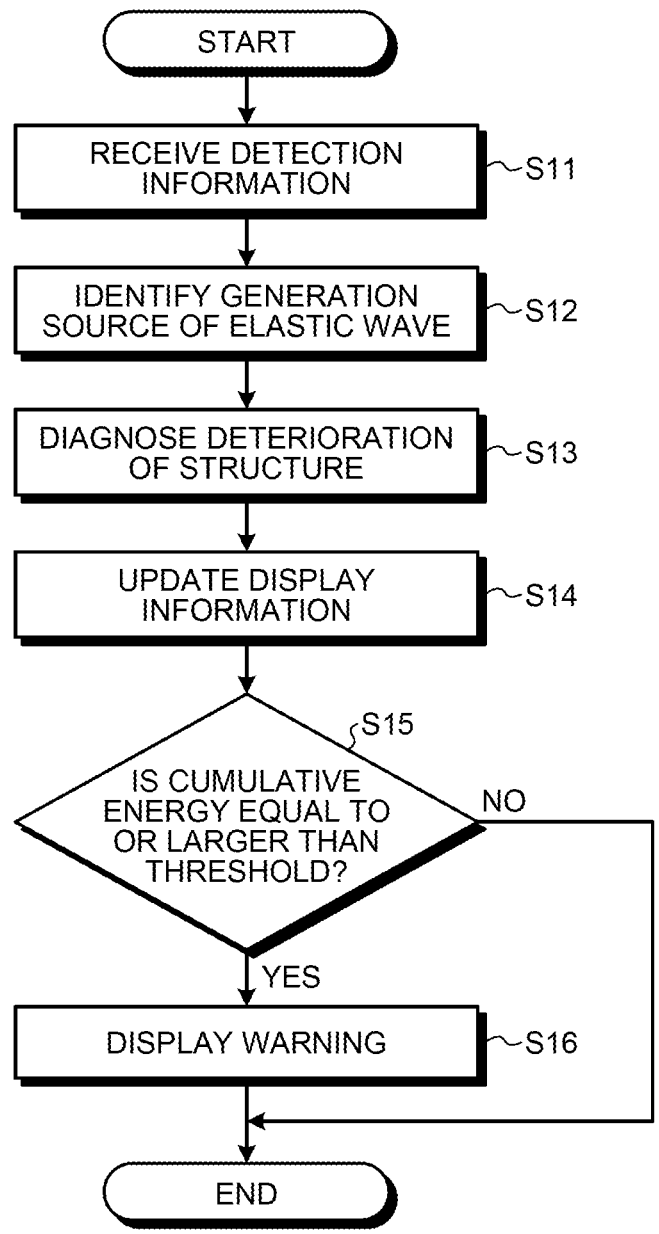
FIG. 15 is a flowchart illustrating exemplary operation of the server according to the embodiment.

FIG. 15 is a flowchart illustrating an operation example of the server 30 according to the embodiment. The communicator 31 receives the detection information from the signal processing apparatus 10 (step S11).

The identifier 33 identifies the position information about the generation source of the elastic wave on the basis of the detection information (step S12). Specifically, the identifier 33 calculates the similarities of the pieces of feature amount information included in the respective pieces of detection information, and classifies the pieces of detection information into groups on the basis of whether the similarity of the feature amount information is equal to or larger than a certain threshold. The identifier 33 calculates the time difference information about the reception times of the AE signals among the four AE sensors 3 by comparing the respective pieces of time information associated with the corresponding pieces of feature amount information (the pieces of feature amount information included in the pieces of detection information classified into the same group) each having a similarity equal to or larger than the certain threshold. The identifier 33 identifies the position information about the generation source of the elastic wave on the basis of the position information about the four AE sensors 3, the time difference information, and the propagation velocity of the elastic wave.

The diagnosis unit 34 diagnoses the deterioration of the structure on the basis of the detection information and the position information (step S13). Specifically, the diagnosis unit 34 diagnoses the deterioration of the structure by determining whether the generation source is present the cumulative energy of elastic wave of which is equal to or larger than a certain threshold. The diagnosis unit 34 generates the diagnosis result information that indicates the diagnosis result.

The display controller 35 updates the display information to be displayed on the display device on the basis of the detection information, the position information, and the diagnosis result information (step S14). Examples of the display information are illustrated in FIGS. 11 and 12.

If the cumulative energy is equal to or larger than the threshold (Yes at step S15), the display controller 35 displays a warning that indicates that the degree of deterioration of the structure is large on the display device (step S16). If the cumulative energy is smaller than the threshold (No at step S15), the processing ends.

The following describes an exemplary hardware structure of the server 30 according to the embodiment.

Figure 16:
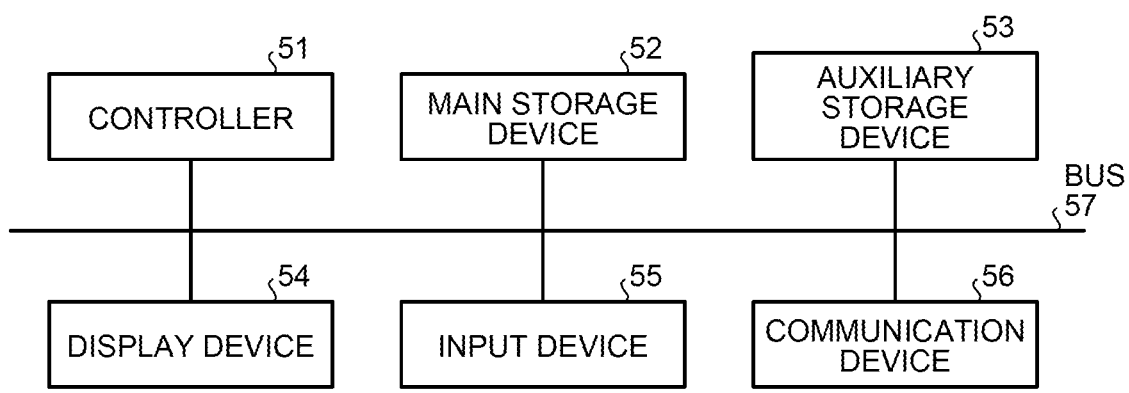
FIG. 16 is a schematic diagram illustrating an exemplary hardware structure of the server according to the embodiment.

FIG. 16 is a schematic diagram illustrating an exemplary hardware structure of the server 30 according to the embodiment. The server 30 according to the embodiment includes a controller 51, a main storage device 52, an auxiliary storage device 53, a display device 54, an input device 55, and a communication device 56. The controller 51, the main storage device 52, the auxiliary storage device 53, the display device 54, the input device 55, and the communication device 56 are connected to one another via a bus 57. The server 30 is a personal computer or a smart device, for example.

The controller 51 executes a program read in the main storage device 52 from the auxiliary storage device 53. The main storage device 52 is a memory such as a read only memory (ROM) or a random access memory (RAM). The auxiliary storage device 53 is a hard disk drive (HDD) or an optical drive. The memory 32 in FIG. 6 corresponds to the main storage device 52 and the auxiliary storage device 53.

The display device 54 displays a state of the server 30, for example. The display device 54 is a liquid crystal display, for example. The input device 55 is an interface for operating the server 30. The input device 55 is a keyboard or a mouse. When the server 30 is a smart device such as a smartphone or a tablet terminal, the display device 54 and the input device 55 may be a touch panel. The communication device 56 is an interface for connection to the network 2.

The program executed by the server 30 according to the embodiment is recorded and provided as a computer program product in a computer-readable storage medium such as a compact disc read only memory (CD-ROM), a memory card, a compact disc recordable (CD-R), or a digital versatile disc (DVD), in an installable or executable file.

The program executed by the server 30 according to the embodiment may be stored in a computer connected to a network such as the Internet, and be provided by being downloaded via the network. The program executed by the server 30 according to the embodiment may be provided via a network such as the Internet without being downloaded.

The program executed by the server 30 according to the embodiment may be embedded and provided in a ROM, for example.

The program executed by the server 30 according to the embodiment has a module structure including the respective functional blocks illustrated in FIG. 6 (the communicator 31, the identifier 33, the diagnosis unit 34, the display controller 35, and the calibrator 36). In actual hardware, the controller 51 reads the program from the storage medium and executes the program. As a result, the respective functional blocks are loaded in the main storage device 52. The respective functional blocks are formed in the main storage device 52. A part or the whole of the respective functional blocks illustrated in FIG. 6 may be achieved by hardware such as an integrated circuit (IC) without using software.

As described above, in the signal processing apparatus 10 according to the embodiment, the time information generator 15 generates the time information having a bit length based on the measurement continuing time period of the structure, the propagation velocity of an elastic wave, and the position identification accuracy of the generation source of the elastic wave. The processor 16 generates the detection information in which the feature amount information indicating the feature of the AE signal and the time information indicating the reception time of the AE signal are in association with each other. The communicator 17 transmits the detection information to the server 30. The signal processing apparatus 10 does not perform, on a structure, the deterioration diagnosis processing based on the AE signal, thereby making it possible to reduce the circuit scale of the signal processing apparatus 10 and to freely change the deterioration diagnosis processing on the structure later. The AE signal is not transmitted but the detection information including the feature amount information is transmitted to the server 30, thereby making it possible to reduce a transmission data amount. This reduction makes it possible to reduce the power consumption of the signal processing apparatus 10. The signal processing apparatus 10, thus, can be operated by a solar battery or a vibration power generation module, for example. As a result, the signal processing apparatus 10 can be installed in a place where no power source is available.

The conventional techniques, however, limit a place in which a signal processing apparatus can be installed, and fail to flexibly change contents of deterioration diagnosis processing of the structures, which processing is based on the AE signal.

While a certain embodiment has been described, the embodiment has been presented by way of example only, and is not intended to limit the scope of the inventions. Indeed, the novel embodiment described herein may be embodied in a variety of other forms; furthermore, various omissions, substitutions and changes in the form of the embodiment described herein may be made without departing from the spirit of the inventions. The accompanying claims and their equivalents are intended to cover such forms or modifications as would fall within the scope and spirit of the inventions.

What is claimed is:

1. A signal processing apparatus, comprising:
a receiver configured to receive a voltage signal from a sensor that detects an elastic wave generated from a structure;
a time information generator configured to generate time information that indicates a reception time of the voltage signal, the time information having a bit length that satisfies b≥$\log_2$ (y×v/dr), where b is the bit length, y is a measurement continuing time period of the structure, v is a propagation velocity of the elastic wave, and dr is a position identification accuracy of a generation source of the elastic wave;
a processor configured to generate detection information in which feature amount information that indicates a feature of the voltage signal and the time information are in association with each other; and
a communicator configured to transmit the detection information to a server.

2. The apparatus according to claim 1, wherein the processor includes:
a gate signal generator configured to generate a gate signal that indicates whether a waveform of the voltage signal continues;
an extractor configured to extract, on the basis of the gate signal, the feature amount information when the waveform of the voltage signal continues; and
a determiner configured to determine the reception time on the basis of the time information and the gate signal.

3. The apparatus according to claim 1, wherein the feature amount information includes at least any one of an amplitude of the waveform of the voltage signal, energy of the waveform of the voltage signal, a rise time period of the gate signal, a continuing time period of the gate signal, a frequency of the voltage signal, and zero-crossing counts of the voltage signal.

4. A server, comprising:
a communicator configured to receive detection information in which feature amount information that indicates a feature of an acoustic emission signal representing an elastic wave generated from a structure and time information that indicates a reception time of the acoustic emission signal are in association with each other;
a memory configured to store therein the detection information; and
an identifier configured to identify position information about a generation source of the elastic wave on the basis of the detection information,
wherein the time information has a bit length that satisfies b≥$\log_2$ (y×v/dr), where b is the bit length, y is a measurement continuing time period of the structure, v is a propagation velocity of the elastic wave, and dr is a position identification accuracy of a generation source of the elastic wave.

5. The server according to claim 4, wherein the identifier:
calculates similarities of pieces of the feature amount information,
calculates time difference information about the reception times of the voltage signals among a plurality of acoustic emission sensors by comparing pieces of the time information associated with the corresponding pieces of feature amount information each having the similarity equal to or larger than a certain threshold, and
identifies the position information about the generation source of the elastic wave on the basis of position information about the acoustic emission sensors, the time difference information, and the propagation velocity of the elastic wave.

6. The server according to claim 5, wherein
the memory further stores therein propagation velocity information in which a material of the structure and a propagation velocity of the elastic wave are in association with each other, and
the identifier determines the propagation velocity of the elastic wave by referring to the propagation velocity information.

7. The server according to claim 4, further comprising a display controller configured to perform control to display, on a display, position information about the elastic wave and cumulative information that indicates cumulative energy of the elastic wave in accordance with the position information.

8. The server according to claim 5, further comprising a calibrator configured to cause the acoustic emission sensors to operate as vibration generation sources and to calibrate the position information about the acoustic emission sensors or the propagation velocity of the elastic wave on the basis of the detection information that includes pieces of the feature amount information each indicating a feature of a voltage signal representing an elastic wave generated from the corresponding vibration generation source.

9. A detection system, comprising:
a plurality of acoustic emission sensors;
a signal processing apparatus; and
a server,
wherein the acoustic emission sensors each includes:
a detector configured to detect, as a voltage signal, an elastic wave generated from a structure,
the signal processing apparatus includes:
a receiver configured to receive the voltage signals from the acoustic emission sensors;
a time information generator configured to generate time information that indicates a reception time of the voltage signal, the time information having a bit length that satisfies b≥$\log_2$ (y×v/dr), where b is the bit length, y is a measurement continuing time period of the structure, v is a propagation velocity of the elastic wave, and dr is a position identification accuracy of a generation source of the elastic wave;
a processor configured to generate detection information in which feature amount information that indicates a feature of the voltage signal and the time information are in association with each other; and
a transmitter-configured to transmit the detection information to the server, and the server includes:
a receiver-configured to receive the detection information from the signal processing apparatus;
a memory configured to store therein the detection information; and
an identifier configured to identify a position of the elastic wave on the basis of the detection information.

10. A signal processing method performed by a signal processing apparatus, the method comprising:
receiving a voltage signal from an acoustic emission sensor that detects an elastic wave generated from a structure;
generating time information that indicates a reception time of the voltage signal, the time information having a bit length that satisfies b≥$\log_2$ (y×v/dr), where b is the bit length, y is a measurement continuing time period of the structure, v is a propagation velocity of the elastic wave, and dr is a position identification accuracy of a generation source of the elastic wave;

generating detection information in which feature amount information that indicates a feature of the voltage signal and the time information are in association with each other; and transmitting the detection information to a server.

11. A signal processing apparatus, comprising:

a receiver configured to receive a voltage signal from a sensor that detects an elastic wave generated from a structure;

a time information generator configured to generate time information indicative of a reception time of the voltage signal, the time information having a bit length b that satisfies b≥log 2 (y×v/dr), where y is a measurement continuing time period of the structure, v is a propagation velocity of the elastic wave, and dr is a position identification accuracy of a generation source of the elastic wave; and a communicator configured to transmit the time information to a server.

12. A server, comprising:

a communicator configured to receive time information indicative of a reception time of an acoustic emission signal representing an elastic wave generated from a structure; and a memory configured to store therein the time information, wherein the time information has a bit length b that satisfies b≥log 2 (y×v/dr), where y is a measurement continuing time period of the structure, v is a propagation velocity of the elastic wave, and dr is a position identification accuracy of a generation source of the elastic wave.

13. A detection system, comprising:

a plurality of acoustic emission sensors;

a signal processing apparatus; and a server, wherein the acoustic emission sensors each comprises:

a detector configured to detect, as a voltage signal, an elastic wave generated from a structure, the signal processing apparatus comprises:

a receiver configured to receive the voltage signal from the acoustic emission sensors;

a time information generator configured to generate time information indicative of a reception time of the voltage signal, the time information having a bit length b that satisfies b≥log 2 (y×v/dr), where y is a measurement continuing time period of the structure, v is a propagation velocity of the elastic wave, and dr is a position identification accuracy of a generation source of the elastic wave; and a communicator configured to transmit the time information to the server; and the server comprises:

a communicator configured to receive the time information from the signal processing apparatus; and a memory configured to store therein the time information.

14. A signal processing method performed by a computer, the method comprising:

receiving a voltage signal from an acoustic emission sensor that detects an elastic wave generated from a structure;

generating time information indicative of a reception time of the voltage signal, the time information having a bit length b that satisfies b≥log 2 (y×v/dr), where y is a measurement continuing time period of the structure, v is a propagation velocity of the elastic wave, and dr is a position identification accuracy of a generation source of the elastic wave; and transmitting the time information to a server.

* * * * *